(12) United States Patent
Kumar et al.

(10) Patent No.: US 9,039,777 B2
(45) Date of Patent: May 26, 2015

(54) MODULAR JUNCTION SEAL OF AN ORTHOPEDIC IMPLANT

(71) Applicant: Biomet Manufacturing, LLC, Warsaw, IN (US)

(72) Inventors: Mukesh Kumar, Warsaw, IN (US); Robert M. Ronk, Pierceton, IN (US); Daniel E. Williamson, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/152,161

(22) Filed: Jan. 10, 2014

(65) Prior Publication Data
US 2014/0180429 A1   Jun. 26, 2014

Related U.S. Application Data

(62) Division of application No. 13/366,510, filed on Feb. 6, 2012, now Pat. No. 8,663,327.

(51) Int. Cl.
| | | |
|---|---|---|
| *A61F 2/30* | (2006.01) | |
| *A61F 2/32* | (2006.01) | |
| *A61F 2/40* | (2006.01) | |
| *A61F 2/36* | (2006.01) | |

(52) U.S. Cl.
CPC ..... *A61F 2/3609* (2013.01); *A61F 2002/30332* (2013.01); *A61F 2002/30589* (2013.01); *A61F 2002/30682* (2013.01); *A61F 2002/365* (2013.01)

(58) Field of Classification Search
CPC .............. A61F 2/38; A61F 2/28; A61F 2/32; A61F 2220/0033
USPC .............. 623/16.11, 18.11, 22.11, 20.1, 623/23.4–23.48, 19.11–19.14
See application file for complete search history.

(56) References Cited

U.S. PATENT DOCUMENTS

| | | | |
|---|---|---|---|
| 4,158,893 A | 6/1979 | Swanson | |
| 4,731,088 A | 3/1988 | Collier | |
| 5,030,234 A | 7/1991 | Pappas et al. | |
| 5,514,182 A | 5/1996 | Shea | |
| 5,735,900 A | 4/1998 | Barret et al. | |
| 5,899,942 A | 5/1999 | Berman | |
| 6,132,470 A | 10/2000 | Berman | |
| 7,819,923 B2 | 10/2010 | Stone et al. | |
| 2007/0250175 A1* | 10/2007 | Meridew et al. | ........... 623/22.21 |
| 2010/0023131 A1 | 1/2010 | Crofford et al. | |
| 2010/0249938 A1 | 9/2010 | Gunther et al. | |
| 2011/0202141 A1 | 8/2011 | Metzger et al. | |

OTHER PUBLICATIONS

Jonathan Cluett, M.D., "Steps of a Hip Replacement", available at http://orthopedics.about.com/od/hipkneereplacement/ss/replacement_2.htm, updated Oct. 28, 2010—6 pages.
"Photoinitiated Radical Vinyl Polymerization", 8.2.2 Radical Generation, Dec. 18, 2007, p. 145.
Dymax Material Safety Data Sheet, Article 7108-SR, Apr. 5, 2007.

* cited by examiner

*Primary Examiner* — Jason-Dennis Stewart
(74) *Attorney, Agent, or Firm* — Taft Stettinius & Hollister LLP; Ryan O. White

(57) ABSTRACT

A method of forming an orthopedic implant, the method comprising the steps of providing a first implant component and a second implant component, the first implant component having a stem and a second implant component including a head defining a female taper sized to receive the stem; coupling the stem to the female taper of the head; forming a modular injunction between the stem and head; applying a seal to the modular injunction to limit bodily fluid from contacting the modular injunction; and forming the orthopedic implant.

8 Claims, 4 Drawing Sheets

MODULAR JUNCTION SEAL OF AN ORTHOPEDIC IMPLANT

CROSS-REFERENCE TO RELATED APPLICATIONS

This application is a divisional of U.S. patent application Ser. No. 13/366,510 filed Feb. 6, 2012, and entitled "Modular Junction Seal of an Orthopedic Implant," the disclosure of which is expressly incorporated in its entirety herein by this reference.

TECHNICAL FIELD

The present invention generally relates to a seal for an orthopedic implant, and more particularly, a polymeric seal disposed at the modular junction of an orthopedic implant for reducing or eliminating physiological fluids from the metallic interface.

BACKGROUND OF THE INVENTION

The statements in this section merely provide background information related to the present disclosure and should not be construed as constituting prior art.

Hip arthritis has been found to be a common source of hip pain as the cartilage of the joint begins to wear over time. A layer of cartilage lines the ball and socket of the hip joint and allows the joint to move freely. As the cartilage wears, hip movements can become stiff and painful. If the arthritis becomes severe enough, hip replacement surgery may become necessary.

Hip replacement is a surgical procedure in which the hip joint is replaced by a prosthetic implant. This can be done as a total replacement or a hemi-replacement. In this procedure, a first step is to remove the damaged cartilage and bone. As known to the skilled artisan, the hip joint has two sides comprising a ball (i.e., femoral head) and socket (i.e., acetabulum). To remove the worn out head of the hip joint, the bone is cut and removed. Once removed, the worn out acetabulum, which is part of the pelvis bone, is reamed to scrape away the damaged cartilage and bone. The new socket of the hip replacement can be inserted. To do so, an acetabular component (e.g., "cup") is inserted into the pelvis area by making the socket slightly smaller than the acetabular component to create a press-fit connection.

Once the acetabular component is attached, the ball is supported by an implant inserted into the hollow center of the femur. This becomes the femoral stem. The center of the thigh bone is shaped to accommodate a tight fit with the femoral stem. The stem can be firmly held in the bone with the use of cement, for example, or alternatively the attachment can be press-fit. With the stem inserted into the femur, the ball of the ball-and-socket hip joint can be inserted on top of the stem. Next, the ball-and-stem portion can be inserted into the socket to complete the hip replacement procedure.

Years ago, this procedure was performed with the ball and stem being pre-fabricated as a single unit. However, over time, the two components became modular so different sizes of ball and stems could be made. The ball (or head) was shaped with a tapered bore through which a similarly shaped tapered stem was coupled. With there being modularity between the parts, concerns arose about possible corrosion at the modular interface. As is known, corrosion can occur at the interface between two metallic components formed of different material, especially when the two components rub against one another. To reduce corrosion, the stem was formed of titanium and the head of cobalt chrome, both of which are mostly benign and have been found to be safe in vivo even when in intimate contact. Each material has an inherent passive layer, and generally goes through a known passivation process to prevent corrosion.

Through different studies, it has been found that if a larger sized ball is coupled to a stem, patients can experience better range of motion. This has been found to be important as hip replacement patients are younger and more active following surgery. Another benefit of using a larger sized ball is a reduction in the number of dislocations. So, as the size of the stem remained constant, the diameter of the ball began increasing from 22 mm to 56 mm or greater in some orthopedic implants. However, as the ball size increased, the torque acting on the ball and the tapered stem increased causing movement between the ball and stem. This movement, referred to as micro-motion, began causing fretting corrosion at the tapered injunction as the passive outer layer of material broke down. Liquid, such as bodily fluid, is able to penetrate the injunction and cause the corrosion. Outer barrier layers have not worked at the injunction as these materials tend to break apart in a high stress environment.

As a result, a need exists for a seal to reduce or prevent the penetration of bodily fluids at the taper injunction of orthopedic implants. It is desirable to position the seal at the injunction to prevent, or at least delay, the onset of corrosion at the injunction.

SUMMARY OF THE INVENTION

In accordance with an exemplary embodiment of the present invention, a seal is provided for preventing a bodily fluid from penetrating an orthopedic implant. The seal includes a tapered section adapted to conformingly mate to a stem of a first implant component and a collar section extending from and circumferentially surrounding a portion of the tapered section. The collar section is adapted to mate to a base of a second implant component such that the tapered section and collar section define an opening therethrough configured to receive the first implant component.

In one aspect of this embodiment, the tapered section and collar section of the seal are formed of a polymeric material. The polymeric material can include polyurethane, silicone, polyethylene, polyether ether ketone, polyetherketoneketone, or a combination thereof. In another aspect, the seal can include a ridge integrally formed with the collar section and extending outwardly in a direction opposite the tapered section, the ridge adapted to mate with a groove defined in the collar section. The ridge can be radially disposed from the defined opening. Related thereto, the ridge may comprise a plurality of ridges integrally formed with the collar section.

In another embodiment, an orthopedic implant includes a first implant component including a male tapered portion, a second implant component including a head, the head defining a female taper adapted to receive the first implant component, and a seal comprising a tapered section and a collar section, the tapered section being adapted to conformingly mate to the first implant component and the collar section extending from and circumferentially surrounding a portion of the tapered section and being configured to mate to the second implant component.

In one aspect of this embodiment, the tapered section and collar section define a passageway disposed along an axis through which the male tapered portion is received. In a different aspect, the seal can be formed of a polymeric material where the material includes polyurethane, silicone, polyethylene, polyether ether ketone, polyetherketoneketone, or a combination thereof. In a further aspect, the implant, which may be a hip implant, includes a ridge integrally formed with the collar section and extending outwardly in a direction opposite the tapered section, where the ridge is configured to couple with the head.

In another aspect, the seal defines a passageway adapted to receive the stem, the passageway and female taper being aligned along an axis when the seal mates with the head and the ridge is spaced radially from the axis. A groove can be defined in the head and sized to receive the ridge. Related thereto, the seal can define a passageway adapted to receive the stem, the passageway and female taper being aligned along an axis when the seal mates with the head. The ridge and groove are spaced radially from the axis. In addition, a second ridge can be integrally formed with the collar section and extending outwardly in a direction opposite the tapered section and a second groove can be defined in the head, the second groove being sized to receive the second ridge.

In a different embodiment, a method is provided for forming an orthopedic implant. The method includes providing a first implant component and a second implant component, the first implant component having a stem and a second implant component including a head defining a female taper sized to receive the stem. The method also includes coupling the stem to the female taper of the head, forming a modular injunction between the stem and head, applying a seal to the modular injunction to limit bodily fluid from contacting the modular injunction, and forming the orthopedic implant.

In one form of this embodiment, the applying step comprises providing an un-polymerized material, applying the un-polymerized material at or near the modular junction, polymerizing the un-polymerized material, and forming a polymeric seal at the modular junction. The polymerizing step can comprise exposing the un-polymerized material to air, heat, ultraviolet light, or infrared light. The method can include removing tissue debris near and on the modular junction and removing or wiping dry the bodily fluids before the applying step.

In another form of this embodiment, the applying step can include providing a polymeric seal having a tapered section and a collar section, the collar section extending from and circumferentially surrounding a portion of the tapered section, mating the tapered section of the seal with a tapered portion of the stem, and coupling the collar section to the head. The method can also include aligning a ridge of the collar section with a groove defined in the head and mating the ridge with the groove. In addition, a second ridge of the collar section can be aligned with a second groove defined in the head such that the second ridge is mated with the second groove. The method may also include aligning a ridge of the tapered section with a groove defined in the stem and mating the ridge of the tapered section with the groove defined in the stem.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
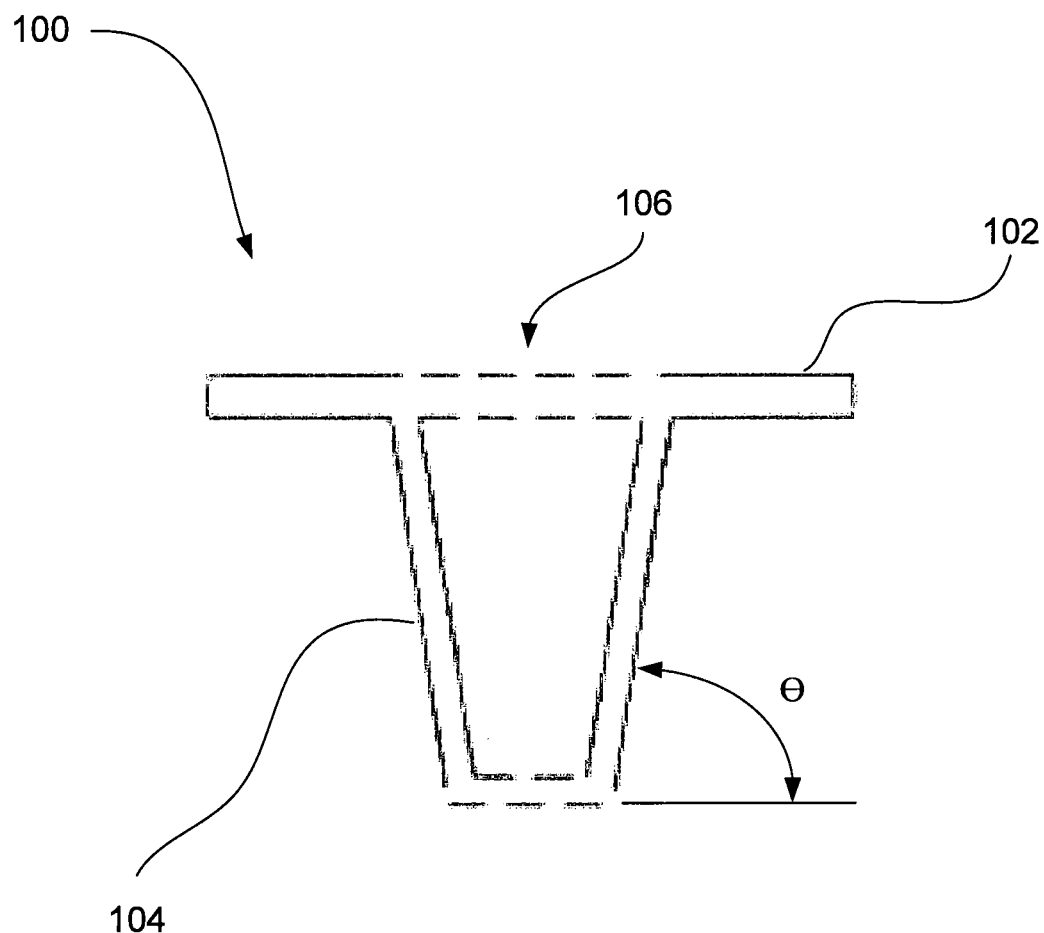
FIG. 1 represents a side view of a seal for an orthopedic implant according to the present teachings.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

Referring to FIG. 1, an exemplary embodiment is provided of a seal 100 for use to prevent or limit bodily fluids from infiltrating the interface between a ball and stem of an orthopedic implant. While the present disclosure refers to a hip prosthesis, including in several of the figures to be described herein, it is to be understood that the teachings of the present disclosure extend to other orthopedic implants for shoulders, knees, etc.

The seal 100 can be shaped to have a flat or collar section 102 and a tapered section 104. The seal 100 can also define an internal channel 106 through which a hip stem, for example, can be inserted. The collar section 102 is adapted to mate with the acetabular head. The tapered section 104 can have surfaces angled by $\ominus°$, where $\ominus$ is between 30° and 90°. The angle $\ominus$ can be designed according to the size and shape of the stem to achieve a desired seal therebetween.

The seal 100 can be formed of different materials as well. For example, the seal 100 can be formed of polyurethane, silicone, polyethylene, polyether ether ketone (PEEK), polyetherketoneketone (PEKK), or a combination thereof. In other words, the seal 100 can be formed of any polymeric material with desired flexibility to sufficiently seal the interface between the stem and ball of an orthopedic implant. As such, the size, shape, and material type are chosen to advantageously reduce or prevent fretting corrosion caused by micro-motion between the stem and ball.

Figure 2:
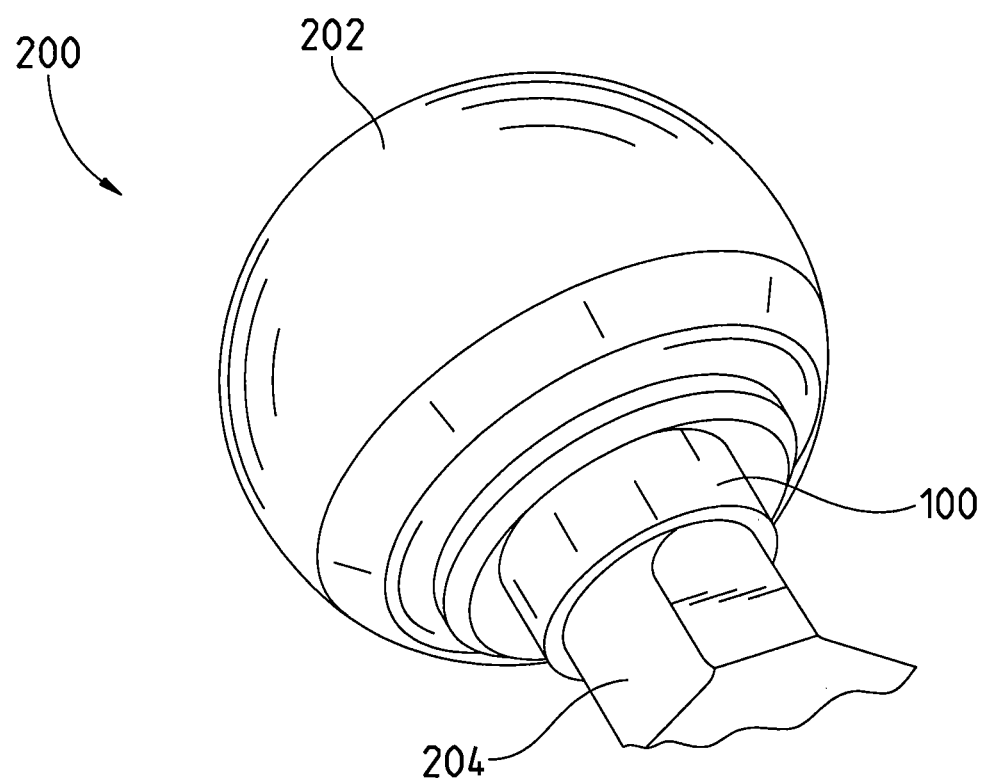
FIG. 2 represents a partial perspective view of an orthopedic implant for a hip replacement.

In FIG. 2, an orthopedic implant 200 for a hip is partially shown. The implant comprises a femoral head 202 for engaging an acetabular cup. The head 202, which is shaped as a ball, includes a tapered bore (not shown) for receiving a hip stem 204. The head 202 can be formed of an alloy such as CoCrMo. The stem 204 can be formed of a titanium material, such as $Ti_6Al_4V$. The interface between the stem 204 and head 202 can be sealed by the polymeric seal 100. To better understand the modular injunction between the head 202 and stem 204, FIGS. 3 and 4 represent embodiments of a hip implant with a polymeric seal.

Figure 3:
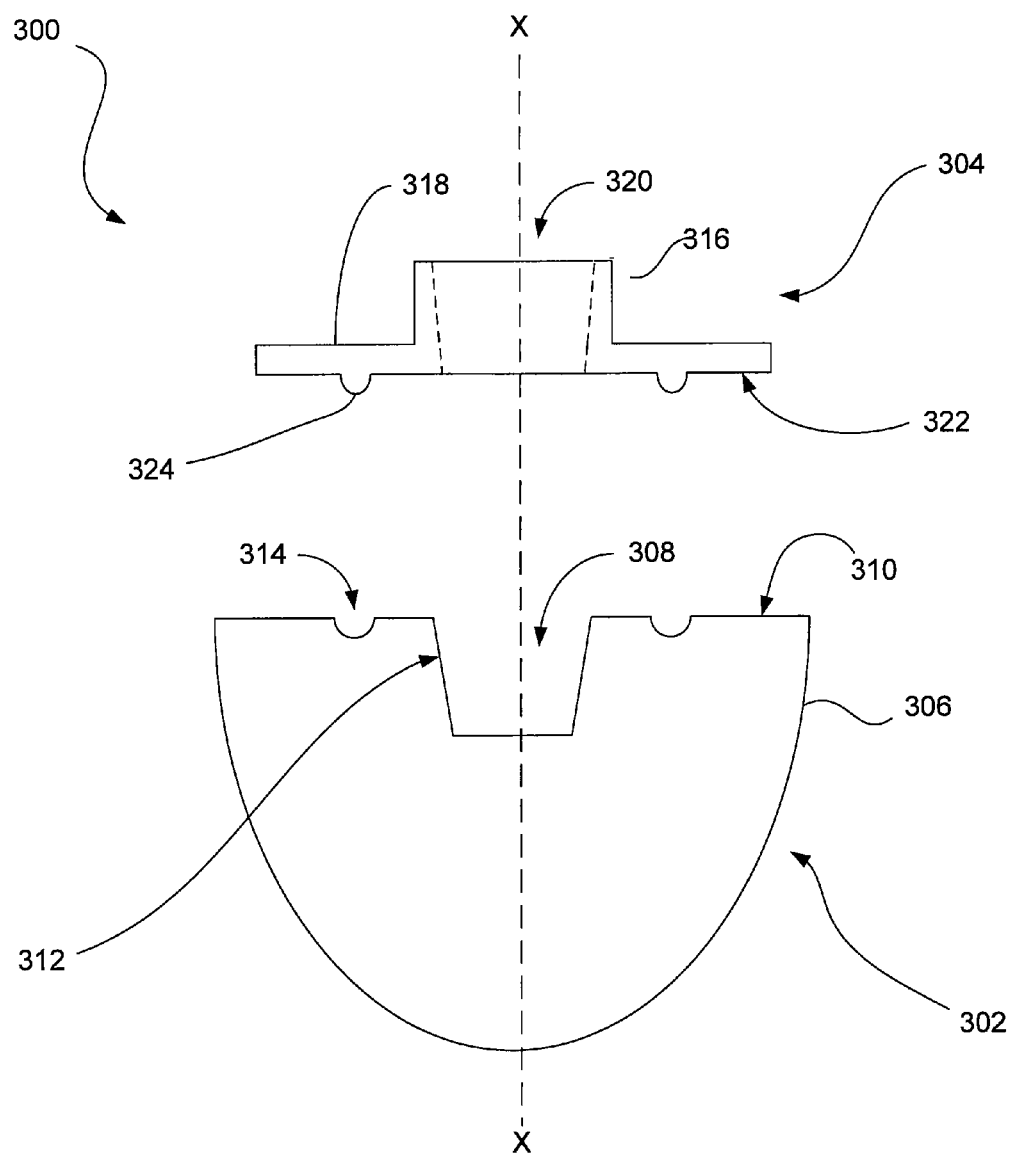
FIG. 3 represents an exploded cross-sectional view of a ball and seal for an orthopedic implant.
Figure 4:
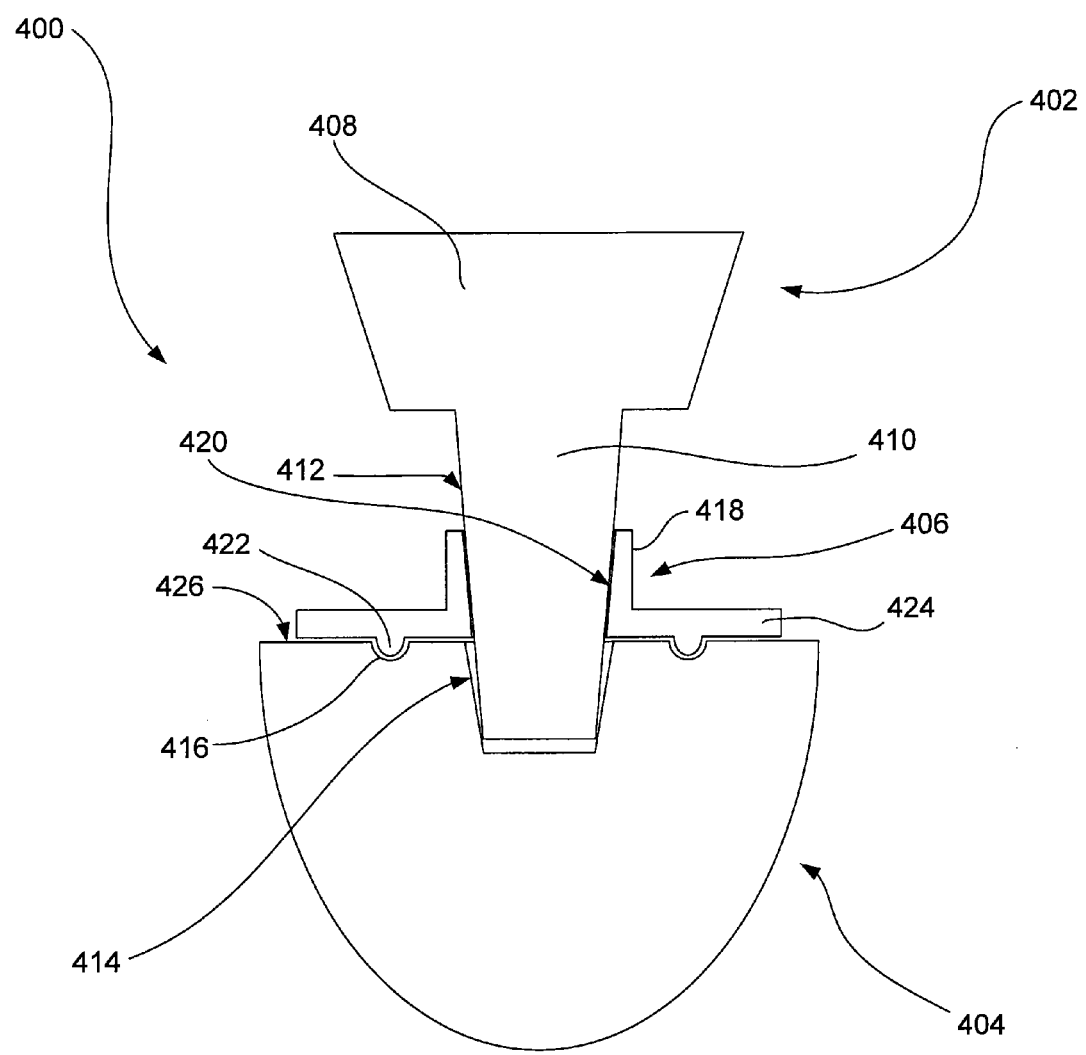
FIG. 4 represents a cross-sectional view of a stem, ball, and seal of an orthopedic implant according to the present teachings.

Referring to FIG. 3, a portion of an orthopedic implant 300 is shown. Here, a femoral head 302 and seal 304 can mate to one another before a hip stem (not shown) is attached. The head 302 includes an outer curved surface 306 that is configured to be received by an acetabular cup. The head 302 forms the ball in the ball-in-socket joint for a hip implant. The head 302 also includes a substantially flat surface 310 for mating with the seal 304. A recess 308 is defined near the center of the head 302 and is adapted to receive the stem. The recess or bore 308 can be formed by a tapered side wall 312 which corresponds to the size and shape of the stem.

The seal 304 can be made from any of the same materials described above. In particular, the seal 304 is made from a polymeric material. The seal 304 can include a collar section 318 and tapered section 316. The collar section 318 includes a surface 322 which mates with the substantially flat surface 310 of the head 302. The seal 304 also includes a tapered channel 320 through which the stem (not shown) is inserted. The tapered walls which define the channel 320 can be designed to correspond to the size and taper of the stem.

As for mating the head 302 and seal 304 to one another, the head 302 can include a groove 314 defined in the substantially flat surface 310. The groove 314 can be formed of any size or shape. In one aspect, the groove 314 can be radially disposed from an axis X-X passing through the center of the head 302. In this aspect, the groove 314 circumscribes the defined bore 308 in the head 302. In another aspect, there can be a plurality of grooves 314 defined in the surface 310. Alternatively, rather than a groove, one or more openings or receptacles can be defined in the surface 310.

The seal 304 can likewise include a ridge 324 defined in a surface 322 of the collar section 318. The ridge 324 can be disposed radially from axis X-X so that the ridge 324 is received by the groove 314 in the head 302. The ridge 324 can have any shape including circular, oval-like, tapered, square, etc. The groove 314 can also include square notches (not shown) to provide a better connection between the groove 314 and ridge 324 when coupled. In this arrangement, any movement between the seal 304 and head 302 can be reduced or eliminated, thus providing a seal to any bodily fluid trying to leak past. In the aspect in which there are multiple grooves 314, the seal 304 can include multiple ridges 324 for coupling to the multiple grooves 314. In another aspect, the ridge or ridges 324 can include latches or notches (not shown) to further engage with the groove 314 to provide a better seal.

Referring to FIG. 4, an orthopedic implant in the form of a hip implant 400 is shown. Here, a hip stem 402 is coupled to a femoral head 404 with a polymeric seal 406 disposed therebetween. The hip stem 402 can include a base portion 408 and a tapered portion 410. The head 404, which is similar to the head 302 of FIG. 3, can include a bore defined in a substantially flat surface 426. The bore can include tapered side walls 414 for accommodating the outer surface 412 of the tapered portion 410 of the stem 402. The tapered portion 410 can be slightly oversized compared to the bore defined in the head 404 to achieve a press-fit connection between the two modular pieces. Cement, glue, or other adhesive can be further used to achieve the connection.

The seal 406, which can be sized and shaped similar to the seal 304 of FIG. 3, can include a collar section 424 and a tapered section 418. A channel is defined in the collar section 424 and tapered section 418 to receive the stem 402. The channel can include tapered walls 420 adapted to correspond to the tapered surface 412 of the stem 402.

Although not shown, the tapered surface 412 can include one or more grooves defined therein. The tapered walls 420 of the seal 406 can include one or more ridges (not shown) to correspondingly mate with these grooves in the stem 402 to achieve a sealed connection.

Alternatively, and as shown in FIG. 4, the surface 426 of the head 404 can define one or more grooves 416 to receive one or more ridges 422 formed in the collar section 424 of the seal 406. The size and arrangement of these grooves 416 and ridges 422 are similar to those shown in FIG. 3. In this aspect, the tapered walls 420 of the seal can be undersized compared to the outer wall 412 of the stem 402 so that when the stem 402 passes through the channel defined in the seal 406, the polymeric material of the seal 406 will stretch to accommodate the oversized stem 402. In this manner, the stem 402 and seal 406 induce a compression fitting therebetween. This compression fitting also does not alter or reconfigure the engagement of the hip stem 402 to the receiving tapered bore (or recess) formed in the acetabular head 404. As such, the head height is not affected by the inclusion of the seal 406.

In addition, the seal 406 and head 404 are sealingly coupled to one another when the ridge 422 is disposed in the groove 416. With the ridge 422 and groove (or, ridges and grooves depending on the embodiment) being aligned with one another, as the stem 402, head 404, and seal 406 are coupled to one another, a seal is formed at the modular injunction to prevent or eliminate possible leakage of bodily fluids into this area and thus limit or delay the onset of corrosion.

In another embodiment, a seal can be formed at the modular injunction rather being pre-made as previously described. In particular, during a hip replacement surgery, for example, the seal can be formed in the operating room using an un-polymerized polymer such as vinyl alkyl ketones (e.g., wavelength of 300 nm or greater), methyl methacrylate (e.g., wavelength of 300 nm or greater), or any monomer that can undergo a chain reaction and thus is amenable to photo-polymerization. Examples of other possible photosensitive monomers include Allyl methacrylate, Barium acrylate, Cinnamyl phthatlate, Diallyl isophtalate, Styrene, Tetrafluoroethylene, and Vinyl cinnamate. A photo-sensitizer can also be added to initiate or assist with the free radical formation that is required for photo-polymerization.

In this embodiment, a surgeon can attach the tapered stem to the metallic head. Once attached, the exposed areas near the interface of the two modular parts can be wiped clean of any debris. The un-polymerized polymeric material can then be applied at and around the interface. Once applied, heat, air, ultraviolet light, or infrared light can be exposed to the un-polymerized material to polymerize it. Alternatively, the method can also include ultrasound as a technique to initiate polymerization. The polymerization method will likely depend on the chemistry of the un-polymerized material.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise.

The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

Furthermore, while the present teachings for the disclosed implant are sometimes described in association with a hip prosthesis, those skilled in the art will appreciate that the present teachings may be incorporated into various other orthopedic implants for a human body such as knee, shoulder, and other joints. Therefore, it is to be understood that the present illustrative embodiments are not meant to limit the present invention.

What is claimed is:

1. A method of forming an orthopedic implant, comprising:
    providing a first implant component and a second implant component, the first implant component having a stem and a second implant component including a head defining a female taper sized to receive the stem, the second implant component having a radially disposed groove;
    coupling the stem to the female taper of the head;
    forming a modular injunction between the stem and head;
    providing a seal having a radially disposed ridge;
    applying the seal to the modular injunction until the ridge becomes at least partially disposed within the groove to limit bodily fluid from contacting the modular injunction; and
    forming the orthopedic implant.

2. The method of claim 1, further comprising removing tissue debris near and on the modular junction and removing or wiping dry the bodily fluids before the applying step.

3. The method of claim 1, wherein the applying step comprises:
    providing a polymeric seal having a tapered section and a collar section, the collar section extending from and circumferentially surrounding a portion of the tapered section;
    mating the tapered section of the seal with a tapered portion of the stem; and
    coupling the collar section to the head.

4. The method of claim 3, further comprising:
    aligning a ridge of the collar section with a groove defined in the head; and
    mating the ridge with the groove.

5. The method of claim 4, further comprising:
    aligning a second ridge of the collar section with a second groove defined in the head; and
    mating the second ridge with the second groove.

6. The method of claim 4, further comprising:
    aligning a ridge of the tapered section with a groove defined in the stem; and
    mating the ridge of the tapered section with the groove defined in the stem.

7. A method of forming an orthopedic implant, comprising:
    providing a first implant component and a second implant component, the first implant component having a stem and a second implant component including a head defining a female taper sized to receive the stem;
    coupling the stem to the female taper of the head;
    forming a modular injunction between the stem and head;
    applying a seal to the modular injunction to limit bodily fluid from contacting the modular injunction; and
    forming the orthopedic implant;
    wherein the applying step comprises:
        providing an un-polymerized material;
        applying the un-polymerized material at or near the modular junction;
        polymerizing the un-polymerized material; and
        forming a polymeric seal at the modular junction.

8. The method of claim 7, wherein the polymerizing step comprises exposing the un-polymerized material to air, heat, ultraviolet light, or infrared light.

* * * * *